United States Patent [19]

Cohen

[11] 4,183,930
[45] Jan. 15, 1980

[54] AMINO DERIVATIVES OF PYRAZOLO [1,5-a]s-TRIAZINE, AND THEIR THERAPEUTIC APPLICATIONS

[75] Inventor: Claude Cohen, Versailles, France

[73] Assignee: Aron S.A., Suresnes, France

[21] Appl. No.: 970,980

[22] Filed: Dec. 19, 1978

[30] Foreign Application Priority Data

Jan. 9, 1978 [GB] United Kingdom ............... 756/78

[51] Int. Cl.² ................. C07D 487/04; A61K 31/53
[52] U.S. Cl. ................................. 424/249; 544/207
[58] Field of Search ..................... 424/249; 544/207

[56] References Cited

U.S. PATENT DOCUMENTS

| 3,846,423 | 11/1974 | Kobe et al. ................... 544/207 |
| 3,995,039 | 11/1976 | Rooney et al. ................ 544/212 |

*Primary Examiner*—John M. Ford
*Attorney, Agent, or Firm*—Young & Thompson

[57] ABSTRACT

This invention relates to compounds having the general formula:

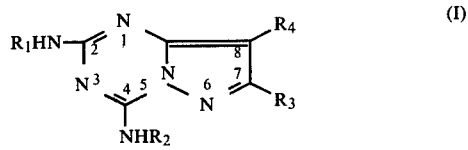

in which:
$R_1$ represents a hydrogen atom or a ($C_{1-4}$) alkyl radical,
$R_2$ represents a hydrogen atom, a ($C_{1-4}$) alkyl radical, a ($C_{2-4}$) alkenyl radical, a ($C_{1-4}$) alkoxy-($C_{1-4}$) alkyl radical or a tetrahydrofuryl- or tetrahydropyranyl-($C_{1-4}$) alkyl radical,
$R_3$ represents a hydrogen atom or a ($C_{1-4}$) alkyl radical, and
$R_4$ represents a hydrogen atom or a ($C_{1-4}$) alkyl radical, and their pharmaceutically acceptable acid addition salts.

Said compounds have valuable bronchodilator properties.

5 Claims, No Drawings

AMINO DERIVATIVES OF PYRAZOLO [1,5-a]s-TRIAZINE, AND THEIR THERAPEUTIC APPLICATIONS

This invention relates to new amino derivatives of pyrazolo[1,5-a]s.triazine, to processes for their preparation and to their therapeutic applications.

A number of amino derivatives of pyrazolo[1,5-a]s.triazine are already known. Thus, 2,4-diamino-7-phenyl-pyrazolo[1,5-a]s.triazine was described by S. Checchi and M. Ridi in Gazz. Chim. Ital., 1957, 87, 597–614.

2-Phenylamino-4-amino-pyrazolo[1,5-a]s.triazine was described by Vogel in Helvetica 1957, 58, 761–771.

On the other hand, various 4-amino-pyrazolo[1,5-a]s.triazines having a nitrogen-containing heterocyclic substituent at 8-position are described in U.S. Pat. No. 3,995,039. Said compounds are described as being bronchodilator agents.

This invention relates to compounds having the general formula:

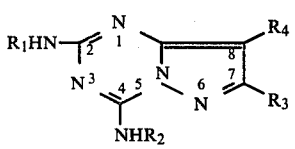

in which:
- $R_1$ represents a hydrogen atom or a $(C_{1-4})$alkyl radical,
- $R_2$ represents a hydrogen atom, a $(C_{1-4})$alkyl radical, a $(C_{2-4})$ alkenyl radical, a $(C_{1-4})$alkoxy-$(C_{1-4})$alkyl radical or a tetrahydrofuryl- or tetrahydropyranyl-$(C_{1-4})$ alkyl radical,
- $R_3$ represents a hydrogen atom or a $(C_{1-4})$alkyl radical, and
- $R_4$ represents a hydrogen atom or a $(C_{1-4})$alkyl radical, and their pharmaceutically acceptable acid addition salts.

Among the compounds of the formula (I) are preferred those in which $R_1$ is a hydrogen atom and $R_3$ is a $(C_{1-4})$-alkyl radical and more particularly those in which $R_3$ is a methyl radical. The acid addition salts may typically be those formed with hydrochloric, sulfuric, phosphoric, methanesulfonic, maleic, succinic, pamoic, acetic, fumaric, lactic, aspartic and citric acids.

The compounds of the formula (I) in which $R_1=H$ may be prepared by reacting an aminopyrazole having the formula:

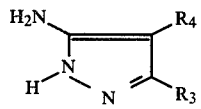

in which $R_3$ and $R_4$ have the above-defined meanings, with a cyanoguanidine having the formula:

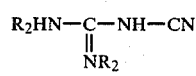

in which $R_2$ has the above-defined meaning. The reaction may be effected by heating, within a solvent such as water, an alcohol or an aromatic solvent. The compounds of the formula (I) in which $R_1=H$ and $R_2=H$ may also be prepared by heating a carboxamidine of the formula:

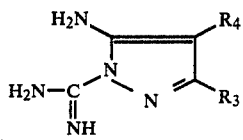

in which $R_3$ and $R_4$ have the above-defined meanings, within a high-boiling solvent such as dimethylformamide, or without solvent.

It is likely that this reaction occurs via the intermediate formation of a compound having the formula:

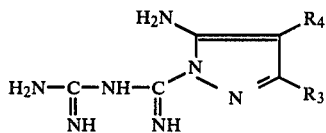

These same compounds of the formula (I) may also be obtained by heating a carboxamidine of the formula (IV) with cyanamide $NH_2$—CN.

The compounds of the formula (I) in which $R_1=H$ and $R_2$ is other than hydrogen may also be prepared by reacting a compound of the formula (I) in which $R_1$ and $R_2$ are hydrogen with an amine $R_2NH_2$ in which $R_2$ has the meaning given for formula (I) and is other than hydrogen, by heating within phenol.

The compounds of the formula (I) in which $R_1$ is other than hydrogen may be prepared by reacting a carboxamidine having the formula:

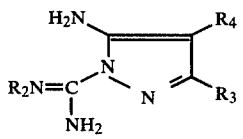

in which $R_2$, $R_3$ and $R_4$ have the meanings given for formula (I), with a compound having the formula:

in which $R_1$ has the meaning given for the formula (I), by refluxing within a solvent such as tetrahydrofuran, according to the technique disclosed by Vogel in Helvetica, 1975, 58, 761–771.

The following non-limiting Examples illustrate the preparation of compounds of the formula (I). In the Examples, the uncorrected melting points were determined with a capillary tube in a Buchi apparatus, the sample being introduced at a temperature 10° C. below its melting point and then heated at a rate of 2° C./mn.

EXAMPLE 1

2,4-Diamino-pyrazolo[1,5-a]s.triazine

In a flask provided with a stirring and a cooling device are mixed 3-amino-pyrazole methane sulfonate (0.1 mole; 17.9 g), cyanoguanidine (0.1 mole; 8.4 g) and water (2 ml).

The resulting mixture is heated, with stirring, at about the refluxing temperature, to give a homogeneous solution; a strongly exothermic reaction is found to occur.

The contents of the flask set to a mass. The material is allowed to cool to 80° C., after which water (10 ml) is added thereto and the whole is again refluxed for fifteen minutes.

After cooling, the resulting solid is filtered off and then washed with acetone. After drying, the crude base is recrystallized from 10 volumes dimethylformamide.

The base is suspended in isopropanol and treated in the hot with one equivalent of isopropanol hydrogen chloride solution. The resulting crude hydrochloride is recrystallized from eight volumes ethanol-water (2:1), to give 13.2 g (68%) 2,4-diamino-pyrazolo[1,5-a]s.triazine hydrochloride crystallized with 0.5 mole water. M.p. (cap.)=282°–283° C.

EXAMPLE 2

(a) 2,4-Diamino-7-methyl-pyrazolo[1,5-a]s.triazine

In a flask provided with a stirring and a cooling device are mixed 5-amino-3-methyl-pyrazole hydrochloride (0.1 mole; 13.3 g), cyanoguanidine (0.1 mole; 8.4 g) and butanol (80 ml).

The resulting mixture is heated, with stirring, at about the refluxing temperature until complete dissolution is obtained, after which an exothermal reaction and recrystallization are found to occur. After cooling, the resulting material is diluted with isopropanol (100 ml), filtered through a Buchner funnel and washed with isopropanol. After drying, the crude base is recrystallized from eight volumes dimethylformamide. The base is suspended in ethanol-water (80:20), after which it is heated to refluxing temperature and one equivalent of isopropanol hydrogen chloride solution is added thereto. Complete dissolution occurs. The hydrochloride crystallizes on cooling. It is recrystallized from ethanol-water (85:15) to give 7.4 g (35%) 2,4-diamino-7-methyl-pyrazolo[1,5-a]s.triazine hydrochloride crystallized with 0.5 mole water. M.p. (cap.)=268°–270° C.

(b) Modification

In a flask provided with a stirring and a cooling device are added 5-amino-3-methyl-pyrazole-1-carboxamidine (0.1 mole; 13.9 g) and dimethylformamide (10 ml) and the mixture is refluxed for one hour. After cooling, water (20ml) is added, the insoluble is filtered off and then recrystallized from dimethyl formamide, to give 1.2 g (14.6%) 2,4-diamino-7-methyl-pyrazolo[1,5-a]s.triazine. M.p. (cap.)=309°–310° C.

EXAMPLE 3

2,4-Diamino-7-ethyl-8-methyl-pyrazolo[1,5-a]s.triazine

In a flask provided with a stirring and a cooling device are mixed 5-amino-3-ethyl-4-methyl-pyrazole hydrochloride (0.05 mole; 8 g), cyanoguanidine (0.05 mole; 4.2 g) and distilled water (1 ml).

The resulting mixture is heated. A strongly exothermic reaction is found to occur. The mixture is allowed to cool to 80° C., after which water (10 ml) is added thereto and it is then refluxed for fifteen minutes. After cooling, the resulting solid is filtered off, dried and recrystallized from dimethylformamide.

The resulting base is suspended in isopropanol and treated in the hot with one equivalent of isopropanol hydrogen chloride solution. The crude hydrochloride thus obtained is recristallized from methanol-water, to give 6 g (49%) 2,4-diamino-7-ethyl-8-methyl-pyrazolo[1,5-a]-s.triazine hydrochloride crystallized with one mole water. M.p. (cap.)=280°–281° C.

EXAMPLE 4

2-Amino-4-methylamino-7-methyl-pyrazolo[1,5-a]s.triazine

In a flask provided with a stirring and a cooling device are mixed 5-amino-3-methyl-pyrazole hydrochloride (0.1 mole; 13.3 g), $N_1N_2$-dimethyl-$N_3$-cyanoguanidine (0.1 mole; 11.2 g) and butanol (100 ml).

The mixture is refluxed for 3 hours, with stirring. Crystallization occurs on cooling. The solid material is filtered off, washed with water and dried. The crude base is treated in the hot within isopropanol, with one equivalent of isopropanol hydrogen chloride solution.

The crude hydrochloride is recrystallized from 7 volumes absolute ethanol, to give 8 g (36%) 2-amino-4-methylamino-7-methyl-pyrazolo[1,5-a]s.triazine hydrochloride crystallized with 0.5 mole water. M.p.(cap.)=272°–273° C.

EXAMPLE 5

2,4-Bis-(methylamino)-7-methyl-pyrazolo[1,5-a]s.triazine

In a flask provided with a stirring and a cooling device are added 5-amino-3-methyl-pyrazole-1-(N-methyl-carboxamidine) (0.1 mole; 15.3 g), tetrahydrofuran (250 ml), triethylamine (40 g) and N-methyl-imidocarbonyl dichloride, $CH_3$—N=$CCl_2$, (0.11 mole; 12.3 g), and the mixture is refluxed for 15 hours. After cooling, the resulting material is filtered and the filtrate is brought to dryness. The residue is chromatographed through a column of alumina (eluent: chloroform-ethanol), to give 6.4 g (33.3%) crude product which, on recrystallization from isopropanol, gives 3.7 g (19.2%) 2,4-bis-(methylamino)-7-methyl-pyrazolo[1,5-a]s.triazine. M.p. (cap.)=204° C.

The same compound may be obtained from 2,4-diamino-7-methyl-pyrazolo[1,5-a]s.triazine and methylamine hydrochloride, by heating within phenol, in an autoclave at 250° C.

EXAMPLE 6

2-Amino-7-isopropylamino-7-methyl-pyrazolo[1,5-a]s.triazine

In a flask provided with a stirring and a cooling device are added 2,4-diamino-7-methyl-pyrazolo[1,5-a]s.triazine (0.2 mole; 32.8 g), isopropylamine hydrochloride (0.2 l mole; 19.1 g) and melted phenol (100 g).

The resulting mixture is refluxed and maintained at that temperature for 5 hours. After cooling, water (100 ml), concentrated aqueous sodium hydroxide solution (150 ml) and then methylene chloride (100 ml) are added. The resulting solid material is filtered off, washed with water and dried, to give 22.5 g crude base (55%) which is then converted to the methanesulfonate. This gives 8 g (15%) 2-amino-4-isopropylamino-7-methyl-pyrazolo[1,5-a]s.triazine methane sulfonate. M.p. (cap.)=238°–239° C.

EXAMPLE 7

2-Amino-4-allylamino-7-methyl-pyrazolo[1,5-a]s.triazine

In a flask provided with a stirring and a cooling device are added 2,4-diamino-7-methyl-pyrazolo[1,5-a]s.triazine (0.5 mole; 82 g), allylamine hydrochloride (0.5 mole; 47 g) and melted phenol (140 g).

The mixture is slowly heated to the refluxing temperature (about 180° C.), which temperature is then maintained for 7 hours. After cooling, water (500 ml) is added, followed by concentrated aqueous sodium hydroxide (250 ml; 2.5 moles). The reaction mixture is stirred for 2 hours and the resulting material is filtered off, to give 77.5 g crude base (76%).

The solid material is taken up into 200 ml distilled water and 50 ml concentrated hydrochloric acid. The resulting solution is extracted with ether and is then made alkaline. The solid material thus obtained is filtered off, washed with water, dried and then dissolved in boiling isopropanol. After filtration, one equivalent of isopropanol hydrogen chloride solution is poured over the hot filtrate. The crude hydrochloride is obtained on cooling. On recrystallization from isopropanol, it gives 27 g (21%) 2-amino-4-allylamino-methyl-pyrazolo[1,5-a]s.triazine hydrochloride crystallized with one mole water. M.p. (cap.)=200° C.

The methane sulfonate is obtained from the same base. M.p. (cap.)=178°–179° C.

EXAMPLE 8

2-Amino-4-tetrahydrofurfurylamino-7-methyl-pyrazolo[1,5-a]s.triazine

In a flask provided with a stirring and a cooling device are added 2,4-diamino-7-methyl-pyrazolo[1,5-a]s.triazine (0.15 mole; b 24.6 g), tetrahydrofurfurylamine hydrochloride (0.15 mole; 20.6 g) and melted phenol (150 g).

The mixture is heated to the refluxing temperature at which it is then maintained for 6 hours. After cooling, distilled water (200 ml) followed by concentrated aqueous sodium hydroxide (175 ml) are added, after which the reaction mixture is stirred for 2 hours, and is then allowed to stand overnight. The resulting solid is filtered off, washed with water, dried and recrystallized from ethanol, to give 8.7 g (23%) 2-amino-4-tetrahydrofurfurylamino-7-methyl-pyrazolo[1,5-a]s.triazine. M.p. (cap.)=148°–149° C.

The characteristics of the compounds thus prepared and also of some of the corresponding bases are tabulated in the following Table.

| Ex. | $R_1$ | $R_2$ | $R_3$ | $R_4$ | Form | M.p. (cap.) °C. |
|---|---|---|---|---|---|---|
| 1 | H | H | H | H | base | 318–320 |
| 2 | H | H | $CH_3$ | H | HCl . ½ $H_2O$ | 282–283 |
|   |   |   |   |   | base | 309–310 |
| 3 | H | H | $C_2H_5$ | $CH_3$ | HCl . ½ $H_2O$ | 268–270 |
|   |   |   |   |   | HCl . $H_2O$ | 280–281 |
| 4 | H | $CH_3$ | $CH_3$ | H | base ½ $H_2O$ | 206 |
|   |   |   |   |   | HCl . ½ $H_2O$ | 272–273 |
| 5 | $CH_3$ | $CH_3$ | $CH_3$ | H | base | 204 |

| Ex. | $R_1$ | $R_2$ | $R_3$ | $R_4$ | Form | M.p. (cap.) °C. |
|---|---|---|---|---|---|---|
| 6 | H | $-CH(CH_3)_2$ | $CH_3$ | H | $CH_3SO_3H$ | 238–239 |
| 7 | H | $-CH_2-CH=CH_2$ | $CH_3$ | H | HCl . $H_2O$ | 200 |
|   |   |   |   |   | $CH_3SO_3H$ | 178 |
| 8 | H | $-CH_2-\text{(tetrahydrofuryl)}$ | $CH_3$ | H | base | 148–149 |
| 9 | H | $C_3H_7$ | $CH_3$ | H | HCl | 245–247 |
| 10 | H | $-C(CH_3)_3$ | $CH_3$ | H | HCl | 280–281 |
| 11 | H | $CH_2-CH=CH_2$ | H | H | HCl . ½ $H_2O$ | 155 |
| 12 | H | $CH_2-CH_2-OCH_3$ | $CH_3$ | H | base | 149–151 |
|    |   |   |   |   | HCl . ½ $H_2O$ | 201–202 |
| 13 | $CH_3$ | H | $CH_3$ | H | HCl . ½ $H_2O$ | 265–267 |

The compounds of the formula (I) and their pharmaceutically acceptable acid addition salts have a bronchial relaxant action and anti-allergic properties. They oppose the acetylchlorine-, serotonine- and histamine-induced bronchospasm in the technique according to Konzett and Rossler. They protect against anaphylactic shock in mice and against passive cutaneous anaphylaxis in rats. In view of said properties, they are therapeutically useful, typically in the treatment of asthma.

Results of pharmacological and toxicological tests are given below. In said tests, the compounds of the formula (I) were compared to theophylline as a standard for this pharmacological class.

I–Bronchodilator action (a) Action on the isolated trachea of guinea-pigs

The trachea is prepared according to the technique disclosed by Castillo & De Beer (J. Pharmacol. Exper. Therap. 1947, 90, 104). The organ is submitted to a tensile load of 500 mg. Theophylline and the test compounds are used at the same dosage of 10 γ/ml.

Table I shows the tensile variations obtained, expressed as percent variation with respect to the activity of theophylline (taken as 100%).

TABLE I: Dilatation of the isolated trachea of guinea-pigs

| Compound of Example | % dilatation | Tensile variation (mg) |
|---|---|---|
| 1 | 67 | −60 |
| 2 | 111 | −100 |
| 3 | 111 | −100 |
| 4 | 170 | −153 |
| 5 | 230 | −207 |
| 6 | 220 | −200 |
| 7 | 200 | −180 |
| 8 | 80 | −72 |

-continued

| Compound of Example | % dilatation | Tensile variation (mg) |
|---|---|---|
| Theophylline | 100 | −90 |

(b) Prevention of bronchospasm in anesthetized guinea-pigs

The activity of the compounds of the formula (I) was investigated according to the technique disclosed by Konzett and Rossler (Arch. Exp. Path. Pharmacol., 1940, 195, p. 71, 74).

The dosages capable of providing 100% inhibition ($ED_{100}$) of the spasm induced by acetylcholine (10–20 γ/kg, i.v.), serotonine (5 γ/kg i.v.) and histamine (10 γ/kg, i.v.) are given in Table II.

TABLE II: Prevention of bronchospasm in anesthetized guinea-pigs

| Compound of Example | $ED_{100}$ (mg/kg) |
|---|---|
| 1 | 20–25 |
| 2 | 15–20 |
| 5 | 10 |
| 6 | 5 |
| 7 | 5 |
| Theophylline | 20–25 |

II—Antiallergic properties (a) Protective effect against anaphylactic shock in mice The protective effect against anaphylactic shock was investigated according to the technique disclosed by Duhault and co-workers (Arzneim. Forschung, 1972, II, 1947). Four weeks after sensitization to bovine albumin, intravenous injection of 0.3 mg bovine albumin in mice causes a fatal anaphylactic shock within the 30 minutes which follow said injection.

The protective effect of compounds of the formula (I), on intraperitoneal administration, at a dosage of 100 mg/kg 30 minutes prior to albumin injection is illustrated in Table III.

TABLE III: Protective effect against anaphylactic shock in mice.

| Experiments | Test material | Number of dead animals | % surviving animals |
|---|---|---|---|
| Series 1 | Controls | 16/20 | 20 |
|  | Example 1 | 10/20 | 50 |
|  | Controls | 10/20 | 50 |
| Series 2 | Example 2 | 2/21 | 90.5 |
|  | Theophylline | 4/20 | 80 |
|  | Controls | 15/20 | 25 |
| Series 3 | Example 3 | 6/19 | 68.5 |
|  | Example 4 | 9/20 | 55 |
|  | Example 6 | 12/20 | 40 |
|  | Controls | 14/20 | 30 |
| Series 4 | Example 7 | 2/20 | 90 |
|  | Example 8 | 6/21 | 71 |

(b) Protective effect against passive cutaneous anaphylaxis in rats

The protective effect against passive cutaneous anaphylaxis (PCA) in rats were investigated according to the technique disclosed by Rosenthale and co-workers (J. Pharm. Exp. Therap. 1976, 197, 725–733). Antisera were prepared by sub-cutaneous injection of 1 mg/ml ovalbumin and by intraperitoneal injection of b $30 \times 10^9$/ml Bacillus pertussis. The PCA reaction was visualized on intravenous injection of antigen (ovalbumin) and Evans Blue in rats which had been intradermally administered the antiserum (4 injections in the shaved back of each rat) 72 hours previously. The protective effect obtained on intraperitoneal administration of the compounds at a dosage of 100 mg/kg 30 minutes prior to ovalbumin injection is set forth in Table IV.

TABLE IV : Protective effect against PCA in rats

| Compound of Example | % Protection (with respect to the controls) |
|---|---|
| 1 | 42 |
| 2 | 56 |
| 3 | 92 |
| 4 | 92 |
| 5 | 83 |
| 7 | 71 |
| 9 | 69 |
| 10 | 50 |
| 8 | 54 |
| Theophylline | 72 |

NOTE:
To determine the percent protection, the length of the longest diameter of the spot and the length of the diameter perpendicular thereto are measured. The product is expressed as mm².

$$\% \text{ protection} = \frac{\text{mean value obtained with the controls} - \text{mean value obtained with the test compound}}{\text{mean value obtained with the controls}} \times 100$$

III—Cardiovascular effects

The compounds of the formula (I) were investigated for their cardiovascular properties in anesthetized dogs. They exert a cardiotonic effect which is evidenced by an increase of contractile force and dp/dt, with a moderate increase of the heart rate, and without any toxic effects on the shape of the ECG. They do not change the responses to mediators such as acetylcholine and norepinephrine or to isoprenaline, nor to carotid occlusion. In addition, they have no antihypertensive effects in hypertensive rats.

IV—Effects on the central nervous system

Some compounds of the formula (I), screened in psychopharmacological tests showed: a depressive effect on rotarod test in mice and a potentiation of apomorphine and amphetamine stereotypes. They also antagonize the catatonic state induced by prochlorperazine. This shows that some of the compounds of the formula (I) exert a definite activity at the level of the central nervous system.

V—Toxicity (1) Acute toxicity

Acute toxicity was determined in mice. The data obtained with theophylline are given for comparative purposes.

Following Table V gives the $LD_{50}$ or the number of dead animals at the dosages indicated.

TABLE V

| Compound | Theophylline | Toxicity (mg/kg) Examples | | | | | | | | | | |
| --- | --- | --- | --- | --- | --- | --- | --- | --- | --- | --- | --- | --- |
| | | 1 | 2 | 3 | 4 | 5 | 6 | 7 | 9 | 10 | 11 | 8 |
| $LD_{50}$ p.o. | 350 | 1250 | 900 | 200 | 1000 | 300 | 750 one death | 1200 | 1000 one death | 1000 one death | 1000 one death | 1000 two deaths |
| $LD_{50}$ i.v. | 175 | 250 no death | 380 | | 300 | | | 200 no death | | | | |

(2) Chronic toxicity

Treatments effected orally in rats during a period of time of 3 months with the compounds of examples 1, 2 and 4 at dosages of 25, 100 and 300 mg/kg and in dogs during a period of time of 1 month with the compound of Example 2 at dosages of 20 and 160 mg/kg, produced neither alteration of the biological constants nor histological injury of the various organs.

VI—Clinical tests

The first clinical tests provided the following data:

(1) The good tolerance of compounds of Examples 1, 2 and 4 in humans.

(2) In clinical pharmacology, functional respiratory exploration determinations provided the same bronchodilator effect found in animals.

(3) A favourable effect was noted in asthmatic subjects and in subjects suffering from respiratory insufficiency.

Thus, this invention relates also to a therapeutic composition having, in particular, a bronchodilator effect, containing, as active ingredient, a compound of the formula (I) or a pharmaceutically acceptable acid addition salt thereof, typically in combination with a pharmaceutically acceptable excipient.

Said compositions may be administered by the oral, parenteral or topical routes. Thus, the compositions may be administered as tablets, capsules or suppositories containing each 100, 200 or 500 mg active ingredient; as drinkable solutions; as injectable solutions containing 200 mg active ingredient per ampoule; or as aerosols or syrups.

The daily dosage regimen may vary from 100 to 1500 mg active ingredient.

Having now described my invention what I claim as new and desire to secure by Letters Patent is:

1. A compound selected from the group consisting of the compounds having the general formula:

$$R_1HN-\underset{N^3}{\overset{N^1}{\bigg\langle}}\underset{\underset{NHR_2}{|}}{\overset{}{\bigg\rangle}}\underset{N}{\overset{N}{\bigg\langle}}\overset{R_4}{\underset{R_3}{\bigg\rangle}} \quad (I)$$

in which:
R$_1$ is selected from hydrogen and (C$_{1-4}$)alkyl,
R$_2$ is selected from hydrogen, (C$_{1-4}$)alkyl, (C$_{2-4}$)alkenyl, (C$_{1-4}$) alkoxy-(C$_{1-4}$)alkyl tetrahydrofuryl-(C$_{1-4}$)alkyl and tetrahydropyranyl-(C$_{1-4}$)alkyl,
R$_3$ is selected from hydrogen and (C$_{1-4}$)alkyl, and
R$_4$ is selected from hydrogen and (C$_{1-4}$)alkyl, and a pharmaceutically acceptable acid addition salt thereof.

2. Compounds as claimed in claim 1, wherein R$_1$ is hydrogen and R$_3$ is C$_{1-4}$alkyl.

3. Compounds as claimed in claim 2, wherein R$_3$ is methyl.

4. A therapeutic composition having a bronchodilator action and anti-allergic properties containing a bronchodilator and anti-allergic effective amount of a compound selected from the group consisting of the compounds having the general formula:

$$R_1HN-\underset{N^3}{\overset{N^1}{\bigg\langle}}\underset{\underset{NHR_2}{|}}{\overset{}{\bigg\rangle}}\underset{N}{\overset{N}{\bigg\langle}}\overset{R_4}{\underset{R_3}{\bigg\rangle}} \quad (I)$$

in which:
R$_1$ is selected from hydrogen and (C$_{1-4}$)alkyl,
R$_2$ is selected from hydrogen, (C$_{1-4}$)alkyl, (C$_{2-4}$)alkenyl, (C$_{1-4}$)alkoxy-(C$_{1-4}$)alkyl tetrahydrofuryl- (C$_{1-4}$)alkyl and tetrahydropyranyl-(C$_{1-4}$)alkyl,
R$_3$ is selected from hydrogen and (C$_{1-4}$)alkyl, and
R$_4$ is selected from hydrogen and (C$_{1-4}$)alkyl, and a pharmaceutically acceptable acid addition salt thereof.

5. A process for the treatment of asthma and respiratory insufficiencies which comprises administering to a human in need thereof a therapeutical composition containing a bronchodilator and anti-allergic effective amount of a compound selected from the group consisting of the compounds having the general formula:

$$R_1HN-\underset{N^3}{\overset{N^1}{\bigg\langle}}\underset{\underset{NHR_2}{|}}{\overset{}{\bigg\rangle}}\underset{N}{\overset{N}{\bigg\langle}}\overset{R_4}{\underset{R_3}{\bigg\rangle}} \quad (I)$$

in which:
R$_1$ is selected from hydrogen and (C$_{1-4}$)alkyl,
R$_2$ is selected from hydrogen, (C$_{1-4}$)alkyl, (C$_{2-4}$)alkenyl, (C$_{1-4}$)alkoxy-(C$_{1-4}$)alkyl tetrahydrofuryl- (C$_{1-4}$)alkyl and tetrahydropyranyl-(C$_{1-4}$)alkyl,
R$_3$ is selected from hydrogen and (C$_{1-4}$)alkyl, and
R$_4$ is selected from hydrogen and (C$_{1-4}$)alkyl, and a pharmaceutically acceptable acid addition salt thereof.

* * * * *